US 6,630,799 B2

(12) United States Patent
Fleming et al.

(10) Patent No.: US 6,630,799 B2
(45) Date of Patent: Oct. 7, 2003

(54) RESONANT POWER SUPPLY AND APPARATUS FOR PRODUCING VACUUM ARC DISCHARGES

(75) Inventors: Ray Fleming, Austin, TX (US); Constantin Popa, Round Rock, TX (US)

(73) Assignee: Safe Food Technologies, Inc., Austin, TX (US)

( * ) Notice: Subject to any disclaimer, the term of this patent is extended or adjusted under 35 U.S.C. 154(b) by 0 days.

(21) Appl. No.: 09/809,762

(22) Filed: Mar. 15, 2001

(65) Prior Publication Data

US 2002/0131555 A1 Sep. 19, 2002

(51) Int. Cl.[7] .............................................. H05B 37/02
(52) U.S. Cl. .................. 315/276; 315/205; 315/209 R; 361/38
(58) Field of Search .......................... 363/17, 25, 132, 363/134; 315/276, 205, 209 R; 361/38

(56) References Cited

U.S. PATENT DOCUMENTS

| 2,528,969 A | | 11/1950 | Oppenheimer | |
| 4,651,264 A | * | 3/1987 | Shiao-Chung Hu | 363/18 |
| 5,173,643 A | * | 12/1992 | Sullivan et al. | 315/276 |
| 5,691,603 A | * | 11/1997 | Nilssen | 315/209 R |
| 5,864,212 A | * | 1/1999 | Sullivan | 315/205 |
| 5,949,633 A | * | 9/1999 | Conway | 361/38 |

FOREIGN PATENT DOCUMENTS

| EP | 1 037 510 A2 | 9/2000 |
| EP | 1 047 288 A2 | 10/2000 |
| JP | 61024135 | 2/1986 |
| WO | WO 0 178 469 A2 | 10/2001 |

* cited by examiner

*Primary Examiner*—Bao Q. Vu
(74) *Attorney, Agent, or Firm*—Thompson & Knight, L.L.P.; Aaron A. Weiss

(57) ABSTRACT

The present invention relates to a vacuum arc discharge power supply. The power supply may be a high frequency resonant AC supply or it may be rectified to give resonant DC. The power supply of the present invention may be used in x-ray production, vacuum arc deposition equipment, vacuum metal refining, ion implantation devices, or other applications that perform vacuum arc discharge.

36 Claims, 13 Drawing Sheets

RESONANT POWER SUPPLY AND APPARATUS FOR PRODUCING VACUUM ARC DISCHARGES

TECHNICAL FIELD

The present invention relates to x-ray tube design and x-ray tube power supply design. More particularly, the present invention relates to the development of a high efficiency x-ray source consisting of a fluorescent x-ray tube, and resonant power supply, which relies on plasma within the tube. The present invention further relates to the design of a power supply to achieve enhanced efficiency. This x-ray tube design can then be used in applications such as product irradiation, and more particularly the sterilization of materials such as foodstuffs and medical implements.

BACKGROUND OF THE INVENTION

As public demand for greater safety from potentially harmful microorganisms increases, scientists must come up with more effective and efficient ways of providing safe products and environments. One technique that is well suited to the reduction in the quantities of microorganisms and pests is irradiation.

Irradiation uses relatively high doses of one of several forms of radiation, gamma rays, electron beam (e-beam), or x-rays, to kill microorganisms and pests that may be present in or on a given material. The radiation ionizes atoms that are sometimes part of critical molecules such as DNA and RNA. Damaging key cell components such as these causes the cells to die, and if enough cells are killed, then the organism dies. There are two main forms of irradiation in use today. They are gamma irradiation and e-beam irradiation. Gamma irradiation uses a radioisotope source such as cobalt-60 that emits gamma rays measured in the millions of electron volts (MeV), while e-beam uses an accelerator to accelerate electrons to MeV range energies. Although both technologies have performed well in limited situations, significant improvements are required to make this technology more accessible.

Gamma irradiation has the major drawback of using radioisotope sources. Radioisotopes cannot be turned off and therefore create a disposal hazard. Additionally, there is public perception linking all radioisotopes to atomic bombs and various accidental radiation deaths, as well as fear that the object being irradiated will be contaminated or somehow become radioactive, even if it cannot. All this makes it difficult to sell the public on the benefits on gamma irradiation. The high energy MeV range gamma rays also require a significant amount of shielding, leading to the irradiation facilities being very large, usually requiring their own building with elaborate shielding and convoluted conveyor systems to safely move the product through the high radiation area. It should be noted also that the gamma rays mostly go through the material without loosing much energy, i.e., without creating much ionization. On the positive side, irradiation sources are inexpensive, stable and require no power to produce the radiation. But while the source itself is inexpensive, the irradiation facility itself is expensive-often costing a million dollars or more. Further, due to the nature of the shielding requirements for radioisotopes, the use of gamma irradiation usually requires a completely separate facility from the manufacturer or distributor and thus results in additional expenses associated with shipping, loading, and packing the materials being irradiated. On top of all this, add the burden of meeting US Nuclear Regulatory Commission and associated state regulatory bodies rules for handling radioactive material.

E-Beam irradiation has several major drawbacks as well. The accelerators are expensive (usually in the million to several million-dollar range) and are fairly big requiring a large room or separate building. Further, unlike gamma irradiation that can penetrate through fairly thick materials (even metals), electrons only travel a short distance in most products. For example, a typical e-beam may only penetrate ¼ inch (6 mm) in hamburger meat, and is only effective near the surface of materials composed of heavier atoms such as steel. This lack of penetration depth does lead to a benefit in that it may require less shielding if there is not much secondary x-ray production, but the limitations prevent the technology from being useful in many cases. E-beam technology is also usually part of a separate facility as well, creating the same types of transport problems as gamma facilities. Similarly, accelerators must be licensed with the states and are carefully controlled as one of the more dangerous electronic radiation producing products available.

It is also possible to have electrons from an accelerator shine on a heavy metallic target to produce high-energy x-rays or low-energy gamma rays that can in turn be used much in the same way as gamma irradiation from radioisotopes. Unfortunately, the percentage of e-beam energy converted into x-rays energy is only about 1 percent and the overall efficiency is much less than that. Thus, an e-beam x-ray system could be considered the worst of both worlds in that now heavier shielding is required with a much more expensive and inefficient source. A full-scale commercial irradiation facility built on this principle would pretty much require its own separate power plant. With the source being so inefficient that the technique is not economically viable except as an occasionally used add-on feature to an otherwise useful e-beam system.

Therefore, in light of all these problems, a need exists for a device that: (1) is small enough to be integrated into the sites where they are needed; (2) achieves an optimal penetration depth for the product being treated; (3) is safe enough for use by an average person; (4) uses available power efficiently, and (5) is low in cost.

Low energy x-rays appear to meet most of these requirements since they can be tuned so that a maximum amount of x-ray energy is absorbed in a given product. X-ray tubes and power supplies are small and inexpensive and can be made in a wide variety of sizes. Television sets are one example of small economical x-ray producing device since they contain the high voltage supply, vacuum tube and other components that are necessary at very low cost, but use shielding to minimize x-ray emissions.

A traditional x-ray tube is made of a glass or ceramic envelope and is evacuated to a high vacuum. The envelope usually has an x-ray transparent window, typically made of beryllium, aluminum, or glass. The x-ray tube may have x-ray shielding, cooling, and high voltage insulation incorporated into its design as well. The tube has a filament at one end that is intensely heated so that it easily supplies electrons when a high voltage potential is applied between it and the anode. The anode is typically a large block of metal that normally is copper (due to its heat conduction), with a different target material often brazed to the surface that the electrons strike. The vacuum x-ray tube requires two power supplies: a DC power supply for the filament heating which typically operates at low voltage (0–10 volts typical) and a few watts of power; and a second power supply that provides a high voltage (5–200+ kV) DC supply that may range in power from a few watts to 100 kilowatts or more.

Traditional x-ray tubes, however, still suffer from a number of known problems associated with efficiency. When electrons hit the target material of the x-ray tube, they loose the energy they gained from being accelerated by the high voltage electrical potential existing between the filament and the target anode. Through scattering and ionization, the electrons lose energy by transferring some of it to the atoms in the anode target material. For each scattering and ionization event, x-rays and lower energy light are emitted, creating a spectrum of energy that is made up of a continuum of x-rays given up through scattering, and characteristic x-rays of the target material. The efficiency of the conversion of electrical energy to x-ray energy is sometimes expressed by a simple empirically derived formula of the form $E_x=E*kZV^x$ where $E_x$ is the x-ray energy, E is the electrical energy, k is a constant, Z is the atomic number of the target, V is the voltage, and x is a power generally accepted to be a little less than 2. By using a higher atomic number target material or higher voltage, it is possible to raise efficiency. Tungsten is a very popular target material for this reason, along with its high melting point and reasonably good thermal conductivity. Other heavy atoms have too low a melting point to be optimal in high-energy x-ray tubes. A tungsten target tube operated at 50 kV potential is approximately 0.7% efficient at converting the energy going into the tube to x-ray energy. When one includes the power supply efficiency, the overall energy efficiency for generating x-rays is less than 0.5%, and then the x-ray beam is further reduced by the window diameter or by collimators that typically allow less than one percent of the x-ray flux to be utilized. This combination of factors results in an effective use of the energy applied to the x-ray tube of less than 50 parts per million (0.005%). The result of these inefficiencies is x-ray tubes and power supplies that are very large and expensive and nearly all of the energy applied becomes waste heat. A small cabinet system that holds less than a cubic foot of material would require a 500-kVA transformer, which is a typical size transformer for an entire small business. Ultimately this wasteful use of energy limits who can practically own and operate x-ray systems for vital uses such as in medical imaging equipment, and makes x-ray tubes unfeasible for certain new applications such as the sterilization of food, medical utensils and products, and countless other beneficial applications of x-rays.

In addition, traditional x-ray tubes, as is also the case with common light bulbs, suffer from frequent filament failure. In both x-ray tubes and light bulbs, the filament is usually tungsten or a tungsten alloy. Over time the tungsten is vaporized, weak spots form, and eventually it breaks. Much of the design improvements over the past 100 years have been directed toward ways of improving filament life through better materials, better cleanliness, and the use of higher vacuum. While filament life has improved, tube life times are typically in the hundreds of hours when operated at anywhere near their peak voltage and current specifications. A side affect of the improvements has been to dramatically increase the manufacturing cost.

The traditional x-ray design has also been driven mostly by the x-ray imaging industry, either medical or industrial, leading designers to develop x-ray tubes with very small focal spots on the anode where the electron beam strikes. While this is a very desirable trait for imaging, it is not desirable when a broad beam source is needed for such applications as sterilization of materials, food irradiation, or x-ray fluorescence. The standard x-ray tube design is inherently a point source design and broader beams are achieved by using larger side windows or end window tube designs that have tighter anode to window geometries allowing for a wider angle exit path. The tube still must be moved farther away from the target being irradiated in order to cover larger areas. The incident dose rates drop with the square of the distance from the source, making the traditional designs even less efficient when a broad beam is required.

It has been known for much of this century that a lamp filled with low-pressure vapors will give off x-rays when a high voltage is applied across it, and during the past few decades there has been a lot of experimental and developmental work on flash x-ray or plasma pinch x-ray devices. They produce x-rays through scattering and electron excitation of the vapor and electrodes as well as the plasma pinch effect that occurs when the magnetic field created by the arc collapses. Flash x-ray devices consist of an x-ray tube filled with a low-pressure vapor and a high voltage capacitive discharge power source. Flash x-ray tubes are generally used for taking high-speed x-ray radiographic images in applications such as ballistics. Their power supply topology limits both their frequency and power, limiting their usefulness as a general source of x-rays. Plasma pinch devices, of which the flash x-ray tube is the simplest version, are being studied intensively as a means of compressing nuclear fuel for fusion. Several very high power devices have been produced but the design of their power supplies have still limited them to pulse operation mostly due to the design goal of igniting a plasma with a single pulse and then maintaining it without additional pulses. To date, the power supplies for these devices consist of a high voltage DC power supply that charges high voltage capacitors, and has a switching mechanism to discharge the capacitors through the tube. The pulse can be as short as tens of nanoseconds to several microseconds in duration. The recharge and cycle rates of the capacitive discharge systems are very slow, typically less than ten per second. Faster types can be made, but are usually lower in power. Both the speed and total power limitations are inherent to the charge-discharge cycle of capacitors. This makes flash x-ray unsuitable for medium and high power continuous operation.

What is important about flash x-ray devices and their cousins, laser ablation x-ray sources, is that both have been shown experimentally to have efficiencies that are, when designed properly, four times higher than a traditional x-ray tube, possibly more. Therefore, a need exists for a new way of driving the flash x-ray device that would allow for high continuous power output at high efficiency to meet the needs of the irradiation application. Much in the same way that the world is converting to fluorescent lighting because it is inherently more efficient than tungsten lighting, a need exists for a fluorescent x-ray system.

Although fluorescent x-ray tubes and power supplies have not been commercially developed for purposes of irradiation, some of the principles underlying the present invention have been used in flash lamps and neon lights. A flash lamp is usually designed to emit a bright flash of light or operated at a higher pulse frequency whereby it can look like it is on constantly to the human eye. A neon light operates at line frequency (60 Hz in the US) or with some newer supplies at 20 kHz or more. Either tube is made of glass or quartz and has two electrodes, which are commonly made of tungsten, predominantly for its high melting point and thermal conductivity. The tube is filled with a vapor that may be at several times atmospheric pressure (1 atm.=760 torr) to 20 torr or less. In order to produce free electrons, a high voltage trigger pulse is usually used to ionize the gas. Then it is operated at lower voltage to produce light. With a large amount of vapor present, the vapor becomes very conductive and effectively shorts out as an arc of electricity passes through it. Traditionally, however, the vapor density is so high that the electrons cannot be accelerated to a high enough potential between scatter events to ionize the inner shell electrons or produce x-rays from the scattering. In fact, the normal operating voltage of flash lamps is only high enough to excite electrons in the outer shells that end up emitting light in the visible, UV, or IR wavelengths. Similarly, neon lights typically have power supplies capable of 9 kV or more, but due to the high fill pressure only a few low energy x-rays are produced. Even the higher voltages are typically so low that the few low energy x-rays that may be produced would be absorbed by the glass envelope. In its simplest form, the flash lamp power supply will consist of a circuit to charge a capacitor that discharges when switched on to both trigger and flash the tube.

In continuous operation, a trigger transformer may be used to produce a high voltage arc to start the tube, then a lower voltage supply, which may be DC, or pulsed DC or AC at a variety of frequencies, will be used to drive the tube. A neon light will have a ballast and step-up transformer typically with two secondary windings to generate positive and negative high voltage. The newer high frequency resonant supplies for neon lights convert the line voltage to DC, then produce high frequency (>20 kHz) AC with a resonant inverter and then use a step-up transformer. The front end of these power supplies up to the transformer is also very similar to the electronic ballasts used in fluorescent lighting. These tubes are available in many sizes and shapes, which are conceivably adaptable to fluorescent x-ray tube applications.

Some of the above-mentioned systems use pulsed DC supplies that rely on capacitive discharge. These supplies are frequency limited by the charge and discharge cycles of the capacitors that also limit the life of the supply. Many capacitors also discharge slowly compared to potential speed of an arc, and so are relatively inefficient at producing x-rays. Resonant supplies are commonly used in fluorescent lighting and resonant supplies with a high voltage transformer are available for neon lighting. Even the first stages of many high voltage power supplies have incorporated resonant inverter technology. These high frequency devices can have smaller and more efficient transformers since they move less power per half sine wave, so the overall supply is smaller and more efficient.

In light of all this, a need exists for a new type of x-ray tube that is lower in cost, more efficient, and illuminates a broader area than current technology, while eliminating the troublesome filament. To achieve these goals it is necessary to integrate new and novel approaches for increasing the efficiency of x-ray production, and design a new power supply accordingly to create a design for a new class of x-ray tube and power supply.

Accordingly, the present invention provides a fluorescent x-ray tube and power supply system that overcomes the problem associated with known sources of x-rays.

SUMMARY OF INVENTION

The device in accordance with an embodiment of the present invention consists of a fluorescent x-ray tube powered by a resonant high voltage power supply that is suitable for use in an x-ray irradiation device or other device requiring an x-ray source. The fluorescent x-ray tube consists of an envelope made of quartz or other suitable non-conductive material, with electrodes mounted on opposing sides, and filled with a low-pressure vapor. The high voltage resonant power supply generates high frequency alternating current (AC) or direct current (DC) pulses. Arcs are formed between the electrodes when the potential reaches a high enough voltage, usually at or near the power supplies peak voltage. As the electrons move through the tube they periodically scatter off vapor atoms or molecules in their paths, ionizing the vapor, and losing some or all of their energy in the process. Scattering and ionization result in continuum and characteristic x-ray production. Free electrons and ions will be accelerated by the potential between the electrodes and periodically scatter off vapor atoms until they strike an electrode and produce additional x-rays. The arc in the tube also creates a magnetic field. This field collapses when the arc stops, creating a plasma pinch that also leads to x-ray production.

Another aspect of the present invention involves the improvement of the efficiency gain in the fluorescent x-ray tube. The efficiency gain in the fluorescent x-ray tube is a direct result of the excitation of the atoms that comprise the vapor. Once the pressure in the tube is low enough to sustain a high voltage arc, the mean free path for the electrons is long enough for the free electrons to gain enough energy between collisions to produce x-rays when they are scattered. This also leads to multiple acceleration zones and therefore multiple x-ray producing interactions along the length of the arc path. The plasma pinch phenomenon at the end of an arc is also responsible for a great deal of the radiation output. In one embodiment of the invention, the efficiency gain is at least five times that of a standard vacuum x-ray tube. The fluorescent x-ray tube also operates as a cold cathode device using free electrons from the excited vapor or electrodes thus eliminating the need for the fragile filament.

The operation of the fluorescent x-ray tube is similar in many ways to the most modem designs for fluorescent lamps, neon lights, or flash lamps, except that the vapor pressure is much lower and the voltage much higher. In the operation of these normal everyday lamps, only the outermost electrons from the vapor atoms are excited, so that s they produce light mostly in the UV, visible, and infrared regions. Flash x-ray systems are also fundamentally similar since they use vapor arc discharges to produce x-rays. Flash systems typically have a capacitive discharge-type supply that is generally suitable to pulsed or low frequency, (typically less than 1000 Hz), operation only. To improve the efficiency while reducing size and cost of the power supply, the present invention incorporates high frequency resonant inverter technology into the supply with the addition of a high frequency high voltage transformer. The inherent difficulty to adapting this technology directly to the fluorescent x-ray tubes is designing transformers that are small enough to operate at high frequency, but big enough to incorporate the insulation needed for the high voltage. In addition, making supplies that can deliver more power is a challenge. In order to make this x-ray source useful for an irradiation application, it is necessary to make a supply that is capable of delivering kilowatts of power instead of a few hundred watts, and generating voltages of 50 kV or more. To meet these requirements and overcome the problems with known power supplies the present invention provides in a new class of x-ray source that can produce x-rays with high efficiency and can be operated in a continuous fashion.

In an embodiment of the present invention, it is envisioned that many different vapors will be desirable and could be used within the x-ray tube to satisfy the need for x-rays of different energies under different circumstances. Each element of the periodic table, when ionized, is capable of giving off different characteristic wavelengths or energies of photons, including x-rays. In addition, it must be kept in mind that higher energy x-rays have greater penetration power, which is beneficial for penetrating thicker, higher density, or higher atomic number materials. It is known that the output efficiency of a vacuum x-ray tube is proportional to the atomic (Z) number of the anode material. Likewise, the efficiency of the fluorescent x-ray tube will also have a proportional relationship to the atomic number(s) of the vapor constituents in addition to the electrode element(s).

In addition, it will be appreciated by those familiar with x-ray devices that the fluorescent x-ray tube may be constructed of various materials or have various windows installed that are relatively transparent to the radiation energy required by a specific process or application. The electrodes may also be composed of materials that are common to the art, and may be selected for their characteristic x-rays, atomic number, melting point, thermal conductivity, electrical conductivity, ionization potential, coefficient of expansion, and various other relevant properties.

The fluorescent x-ray tube of the present invention offers vastly improved x-ray production efficiency, a lower production cost for both the x-ray tube and power supply, less heat generation, and it is designed to eliminate the troublesome filament common to existing designs. In addition, the present invention easily configured as a broad beam source, since x-rays are emitted along the entire arc path length. This allows large materials to be placed nearer to the x-ray source, thus minimizing spatial transmission losses in comparison with traditional point source x-ray tubes. In an alternate embodiment, the fluorescent x-ray tube of the present invention can be collimated and/or designed with a short arc gap similar to typical commercially available arc lamps for imaging applications. The expensive DC power supply used in traditional x-ray tubes is replaced with a much lower cost resonant supply, and the x-ray tube itself may be constructed in a much less expensive manner than traditional vacuum x-ray tubes, thus making the invention useful for otherwise cost prohibitive uses.

The fluorescent x-ray tube of an embodiment of the present invention is well suited to the product irradiation application due to its high efficiency and broad beam capabilities. Material that is to be irradiated can be positioned in close proximity to receive x-rays from the tube, in a variety of possible configurations.

In alternate embodiments, the packaging of the irradiation device can also have several embodiments. In one embodiment, the packaging of the device may be a cabinet-type device similar to a microwave oven where product is place inside in order to be treated. In another embodiment the device is built over or around a material conveyance apparatus for continuous or batch treatment much like an airport x-ray scanning system. In a third embodiment, it is a flow through device where the product, such as liquids or air conveyed materials, flow through an area being irradiated. Shielding and safety interlocks are added as needed to protect operators of the equipment and bystanders.

A fluorescent x-ray tube is beneficial for other typical x-ray applications as well, including but not limited to x-ray fluorescence, medical and industrial imaging, medical treatment, and x-ray lithography.

BRIEF DESCRIPTION OF THE DRAWINGS

For a more complete understanding of the present invention and the advantages thereof, reference is now made to the following descriptions taken in conjunction with the accompanying drawings. In the drawings, depicted elements are not necessarily drawn to scale and like or similar elements may be designated by the same reference numeral throughout the several views.

DETAILED DESCRIPTION

Figure 1:
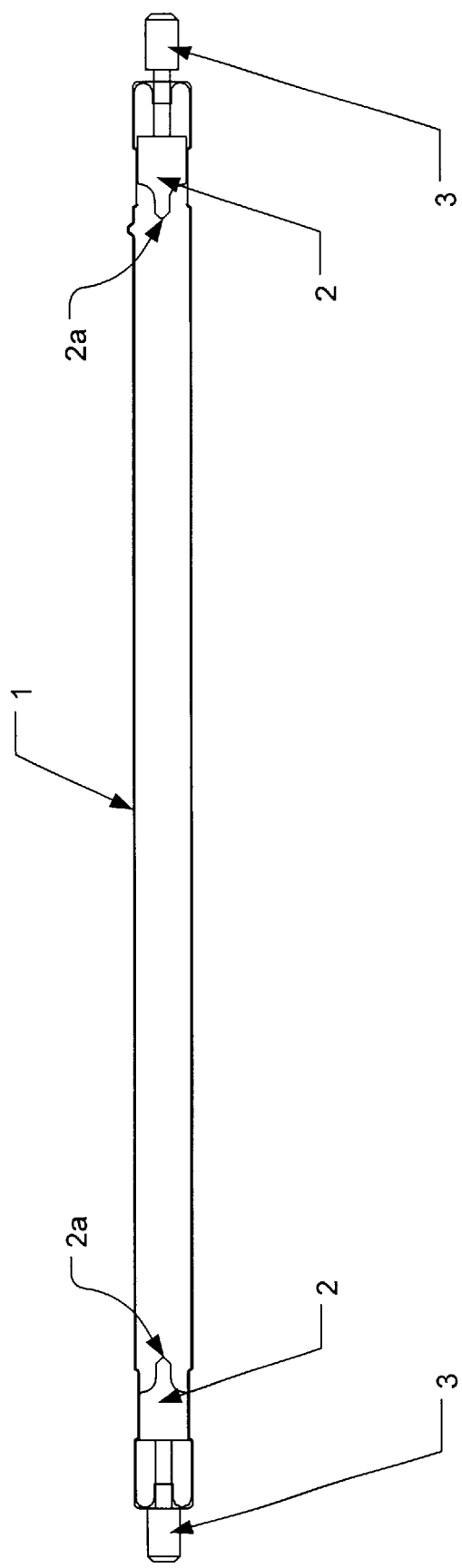
FIG. 1 shows a basic fluorescent x-ray tube design according to the present invention.

According to the present invention, a fluorescent x-ray tube with a resonant power supply is supplied that provides a substantial improvement over existing x-ray tubes. In the most basic description of the operation of an x-ray tube, a pulse of electrons travels through a tube, crosses a gap between the electrodes at either end of the arc path, ionizes the vapor atoms in the path, and creates plasma. Electrons fill the vacant orbitals of vapor atoms and produce photons, including x-rays characteristic to the vapor atoms. X-rays are also produced when electrons that are accelerated by high voltage, scatter off the vapor atoms, which causes them to change directions and emit an x-ray related to their change in direction and energy. Additionally, there are ions being accelerated under the same high voltage toward the electrode and these too can be scattered off other ions, with a resultant production of x-rays. Some collisions will even occur between ions and electrons accelerated in opposite directions capable of producing x-rays at twice the operating potential. Then both electrons and ions strike the electrodes and lose their energy by both scattering and electron excitation, leading to further x-ray generation. Finally the magnetic field created by the arc collapses causing a plasma pinch that gives off additional x-rays.

Vacuum x-ray tubes, flash tubes, and flash x-ray tubes are fundamentally quite similar. The differences lie principally with the fill gas, fill gas pressure, the operating voltage, and power supply topologies. Vacuum x-ray tubes are usually evacuated to $10^{-7}$ torr or less. These tubes must be evacuated to minimize damage to the filament due to ion bombardment. However, due to having a filament, vacuum x-ray tubes do not need vapor for a supply of free electrons. But, by operating a tube in cold cathode mode, i.e. without a heated filament, and using vapor as a source of free electrons one can eliminate the fragile filament from the x-ray source. Both flash tubes and flash x-ray tubes take advantage of this.

According to the present invention, if a typical flash tube is filled to atmospheric pressure with a vapor and then evacuated, as the vapor pressure in the tube drops to below, for example, 10 millitorr (nitrogen calibrated pressure), the tube will sustain a high voltage potential across it, and arcs through the tube produce measurable x-rays. The exact pressure value depends on fill gas, tube length and other aspects of tube construction. It is at this point that the vapor density has dropped low enough (e.g., the mean distance between atoms or molecules of the vapor is large enough) so that the electrons are capable of being accelerated to a high potential between interactions with the vapor atoms, so when they strike the vapor atoms, or the target, x-rays are produced. If the potential across the tube in kV is greater than the potential needed to ionize electrons in orbit around the vapor atoms, characteristic x-rays will be emitted when those orbitals are refilled after ionization.

FIG. 1 illustrates a base fluorescent x-ray tube design that may be used according to the present invention. The basic design of the flash x-ray tube includes a quartz envelope 1, two identical electrodes 2 at either end of the tube, and contacts 3 for connection to a power supply. In an embodiment, the x-ray tube is a Perkin Elmer ILC Model 8610 flash tube filled with xenon gas. Initially, the existing flash tube is filled to a lower than normal pressure. It was found that a fill pressure range of 4 to 7 millitorr (nitrogen calibrated pressure) produced tubes that could sustain voltages in the 8 kV to 120 kV range, and produce measurable x-rays.

According to the invention, a number of different x-ray tube designs are possible. FIG. 1 illustrates a slightly modified version of a standard flash tube design. The original design was intended for DC operation. The cathode was conical in shape while the anode was flat, with each located at either end of the quartz envelope 1. There are also compositional differences to improve operation; such as the elimination of the barium complex in the cathode, as well as using a denser tungsten material. The original cathode design would actually entrain the vapor thus reducing the pressure below the useful range over time. For AC operation, two identical electrodes 2 that have a longer and narrower tip are provided. This gives the tube a more consistent voltage response, minimizes mirroring on the envelope from vaporized tungsten, and also minimizes shadowing in the target area by the electrode itself. Still narrower and/or longer electrodes or hollow cathodes may be preferred for their arc and wear characteristics. It is important to maximize the space between the electrode tips 2a where the arcs strike and the envelope 1 since pinholing of the envelope by the arcs is a common failure mode. The contacts 3 are typical of flash lamp designs.

Figure 2:
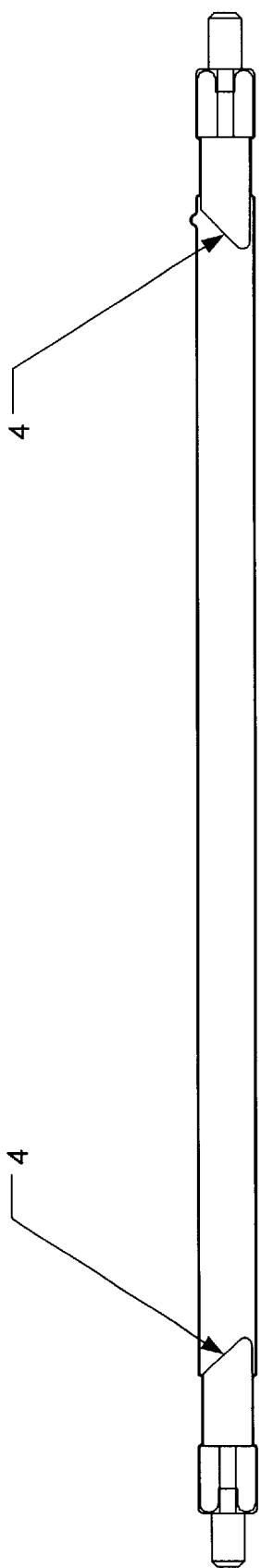
FIG. 2 illustrates an alternative x-ray tube design of the present invention with electrodes with an angular face.

FIG. 2 illustrates an alternate x-ray tube design according to the present invention. As shown in FIG. 2, the electrodes 4 are cut at an angle so that x-rays originating at the electrode can be directed toward the material being irradiated giving a small increase in effective output. This angled cut is common to side window vacuum x-ray tubes. The tip is slightly rounded to prevent it from having a sharp point adjacent to the envelope, but this design could benefit from having a greater electrode to envelope spacing than shown here.

Figure 3:
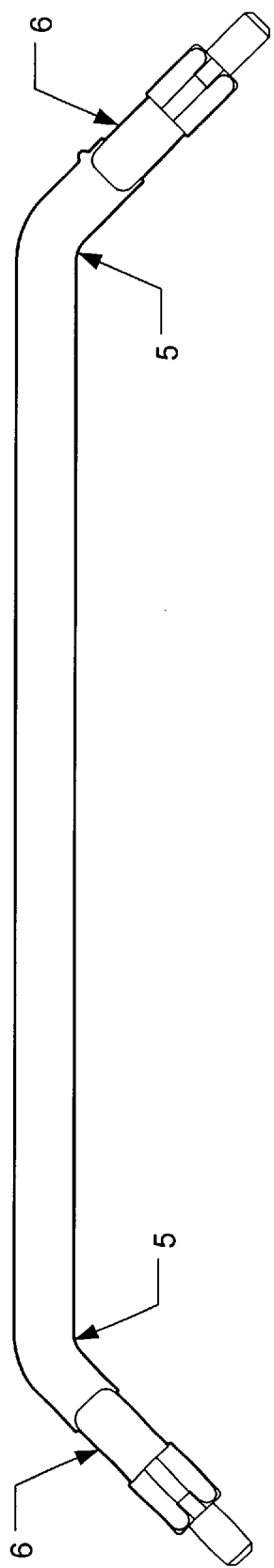
FIG. 3 shows yet another alternative x-ray tube design according to the present invention having bends to angle the electrodes.

FIG. 3 shows yet another alternate x-ray tube design according to the present invention. Instead of cutting the electrode at an angle, FIG. 3 shows a design where the tube has a bend 5 so the electrodes 6 face the direction of the target material. In FIG. 3, only slightly rounded electrodes 6 are shown that are more typical of flash tube designs, but not ideal for fluorescent x-ray tubes. A preferred power supply design provides high frequency alternating current, so both electrodes are typically identical in shape and material. Other designs intended for DC operation may have different electrode shapes and/or material composition, depending on whether they are the cathode or the anode, following design strategies that are common to the art of lamp design. The length of the tubes or electrodes may be varied to achieve many different arc lengths. Such variations are common with flash and arc lamps, and those designs can readily be adapted to fluorescent x-ray use.

According to another aspect of the fluorescent x-ray system of the present invention, multiple x-ray tubes may be used. Multiple tube arrangements are particularly useful for broad beam irradiation applications. Such arrangements allow a large area to be irradiated with the tubes in close proximity with the material, thus minimizing spatial transmission losses (the R squared losses). In a simple variation, several tubes may be powered in a series or parallel arrangement keeping in mind that twice the voltage is needed when two tubes are in series, and additional or somewhat independent parallel circuitry may be needed in the parallel case to ensure that each tube triggers. Multiple arrangements of such modules may be useful in large area or cabinet irradiation devices. It is also possible to integrate multiple electrodes into a single vapor filled envelope to accomplish the same thing and improve the evenness of the illumination by igniting a larger area of vapor.

Figure 4:
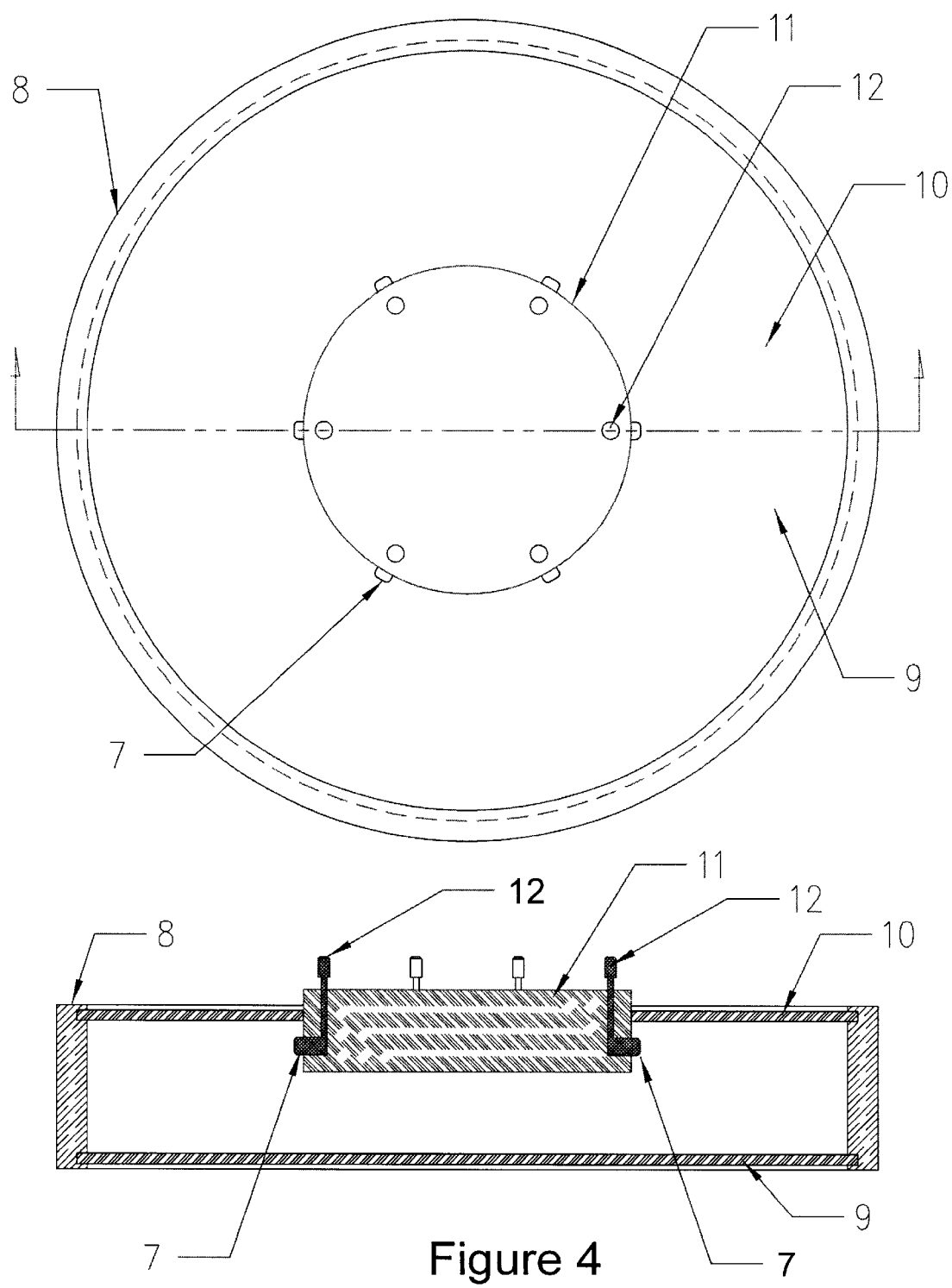
FIG. 4 illustrates a multiple electrode x-ray tube according to an aspect of the present invention.

FIG. 4 illustrates an exemplary multiple tube arrangement. A large circular chamber is provided with a radial arrangement of electrodes 7 and contacts 12. The electrodes are held within an insulating material 11, and attached to the outer circular electrode 8 by another insulating piece 10, which can be all one piece. In an embodiment, the insulating materials (10 and 11) are typically ceramic. However, it should be understood that other insulating materials may be used without departing from the spirit an scope of the present invention. There is a radiation transparent window on the opposite side (9) that must be electrically and mechanically suited to the design in terms of insulation characteristics and mechanical strength as required by the significant vacuum in the tube. One can envision numerous other various ways of arranging the electrodes in a variety of chamber shapes including spherical. The window material may also be the target, simplifying the design somewhat in exchange for the problem of creating a lot of damage to the window during normal use. In alternate embodiments, a linear, radial, or spherical arrangement of electrodes may be designed to produce ion impacts in a central region at effectively twice the applied voltage. These broad area irradiation designs can easily be ten times more efficient geometrically at delivering an x-ray dose over a wide area than a point x-ray source. By also considering the typical 5 to 10 time improvement this invention offers, it is possible to achieve 100 times more efficient use of power over traditional x-ray sources in some applications.

Figure 5:
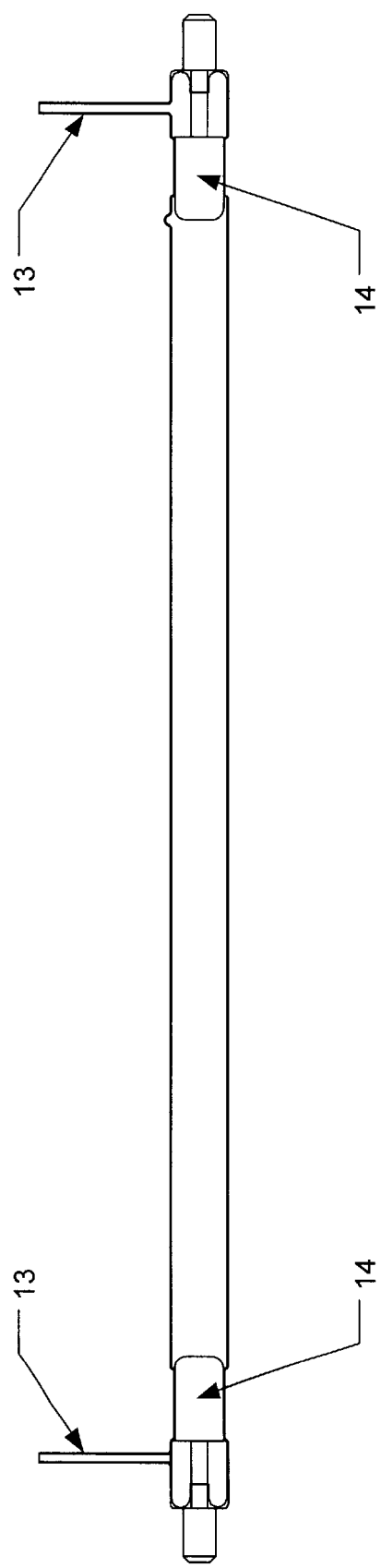
FIG. 5 is a drawing of a gas flow tube design.

FIG. 5 illustrates the use of continuous vapor flow or periodic vapor injection in an x-ray tube. Although this aspect of the present invention is illustrated using a single x-ray tube, these same concepts may be extended to multiple tube arrangements. Gas-puff devices are well documented, but would be difficult to implement at high frequency, although a pulsed device may be preferred in some instances for maintaining proper pressure within the tube. Vapor flow is attractive for its added cooling; its ability to carry away vaporized ions from the envelope or electrodes; and its ability to regulate the tube pressure externally. In its simplest form the envelope will have tubes 13 attached behind both electrodes 14, so one can function as an inlet and the other an outlet. This can improve the longevity of the tube and make it more viable for high output or continuous use applications. It is important to note that the inlet and outlet gas flow connections need to be electrically isolated to prevent arcing as is well-known in the art. It may also be advantageous to have holes drilled through the electrodes to provide for the vapor flow and at the same time make it a hollow cathode design as discussed below.

Figure 6:
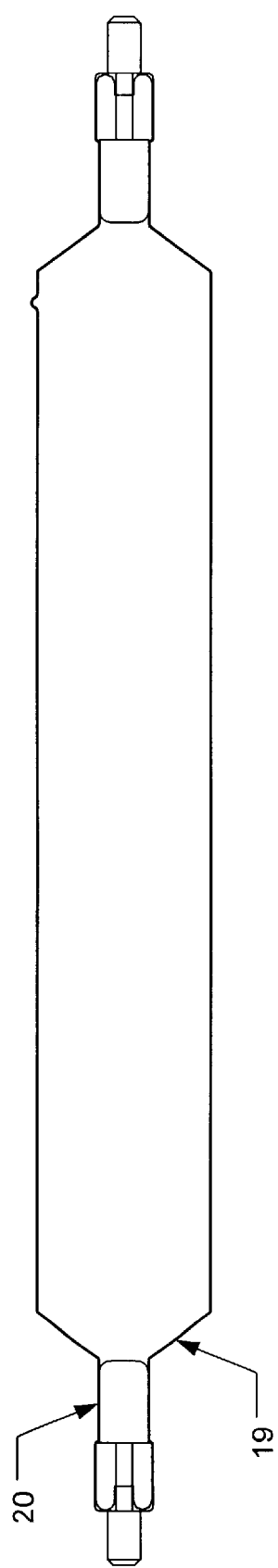
FIG. 6 illustrates an alternative drawing of a tube design according to the present invention with an increased diameter to prevent plating.

Since one of the principle failure mechanisms for a cold cathode tube is due to plating of the electrode material along the tube walls, and ion impacts are the most significant cause of the electrode vaporization, it is possible to extend tube life by controlling the location of the plating so that it does not degrade the x-ray transmission or provide a conductive path along the inside of the envelope. It is possible to reduce the plating along the main body by several techniques. FIG. 6 illustrates one technique for reducing plating according to the present invention. As shown in FIG. 6, the tube diameter 19 is increased in the region just inside the electrodes 20 causing most of the plating to occur in the adjacent area. The arcs occasionally bounce off the envelope at various points along the length of the arc path so a larger diameter is a means to distribute these events over a larger surface area and thus prolong tube life. Increasing the volume can also allow an increase in power by increasing the number of possible ionization events and/or the magnitude of the plasma pinch. One may consider deflecting most of the ions away from the electrodes by designing in a radius that is to tight for them to travel in or to use electrostatic or other deflection devices, but these solutions are not very practical due to the fact that most of the ions come from a region within several millimeters of the electrode.

Figure 7:
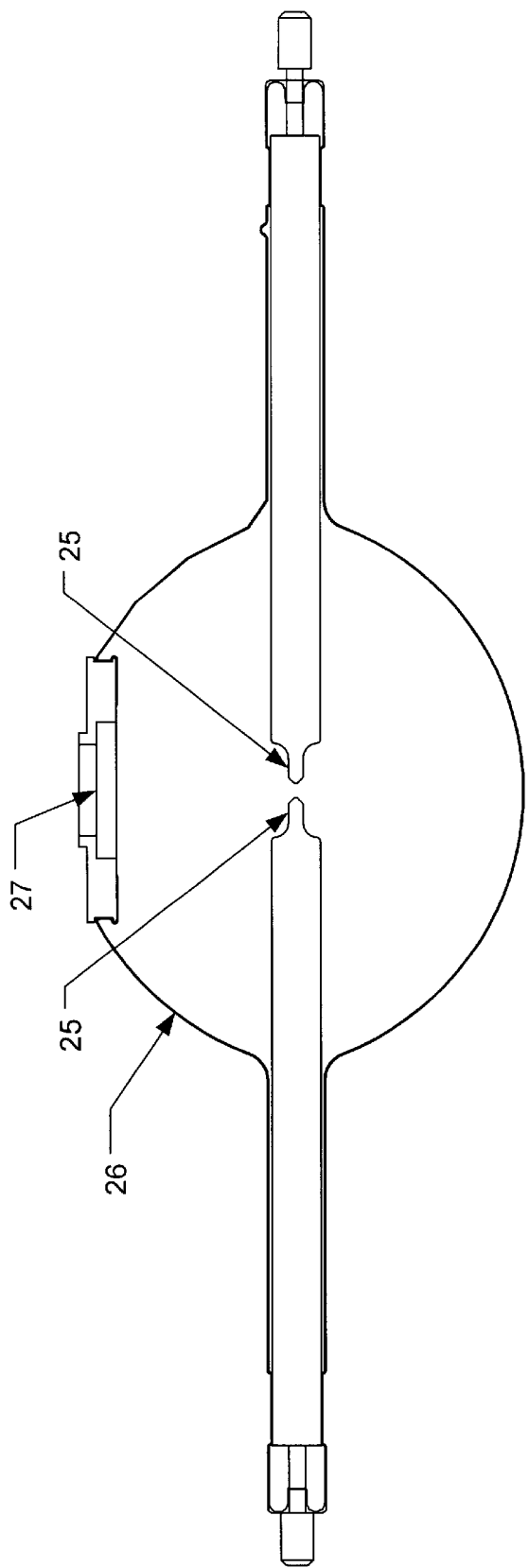
FIG. 7 is a drawing of a short arc path tube with an integrated beryllium window according to another aspect of the present invention.

Just as small arc length arc lamps can be used in focused lighting applications such as spotlights, a small arc length fluorescent x-ray tube may be used according to the present invention for focused x-ray applications such as medical imaging and therapy, industrial radiography, and x-ray lithography applications. FIG. 7 illustrates the use of small length are lamps in an embodiment of the fluorescent x-ray tube of the present invention. Electrodes 25 are located closer together (approximately a 1 mm gap). The envelope 26 has been enlarged in the vicinity of the arc as is typical with an arc lamp. While the lamp can be made with or without a more x-ray transparent window, an embodiment uses drawing illustrates a beryllium window 27 attached to the envelope 26 using a design that is typical of a side window vacuum x-ray tube. A window may be desired when low x-ray energies are needed, in particular below 20 keV. An x-ray window that is relatively transparent to the desired energy may be installed in the tube's envelope. Such windows are typically constructed of thin aluminum, beryllium foil, glass quartz, or other similarly low atomic number material. Window assemblies may also include a ring that may be used for mounting, grounding, and/or collimation.

In the realm of plasma physics, magnetic confinement has been established as a principal method for containing and controlling plasma. The fluorescent x-ray tube is no different. According to one aspect of the present invention, by placing inductive windings around the tube, an increase in the current in the pulse is achieved. Since the arcs are preceded by a buildup of free charges at the electrodes, the inductance of the windings resists the current flow and allows for greater charge buildup and hence higher current when the pulse does occur. The inductor(s) may be passive, having only a fixed resistance, or active, each with its own internal current flow. In its simplest form, one long inductor may extend over the length of the tube with adequate spacing or material composition to be relatively transparent to x-rays. In a preferred embodiment, an inductor is located near the electrodes at each end. Other electrostatic and/or magnetic field generating devices may be used around the tube for the purpose of confining and controlling the arcs. By keeping the arc centered in the tube, potential damage to the envelope is minimized. Additionally, having windings around the tube can provide a means for triggering the tube, or controlling the triggering voltage.

Figure 13:
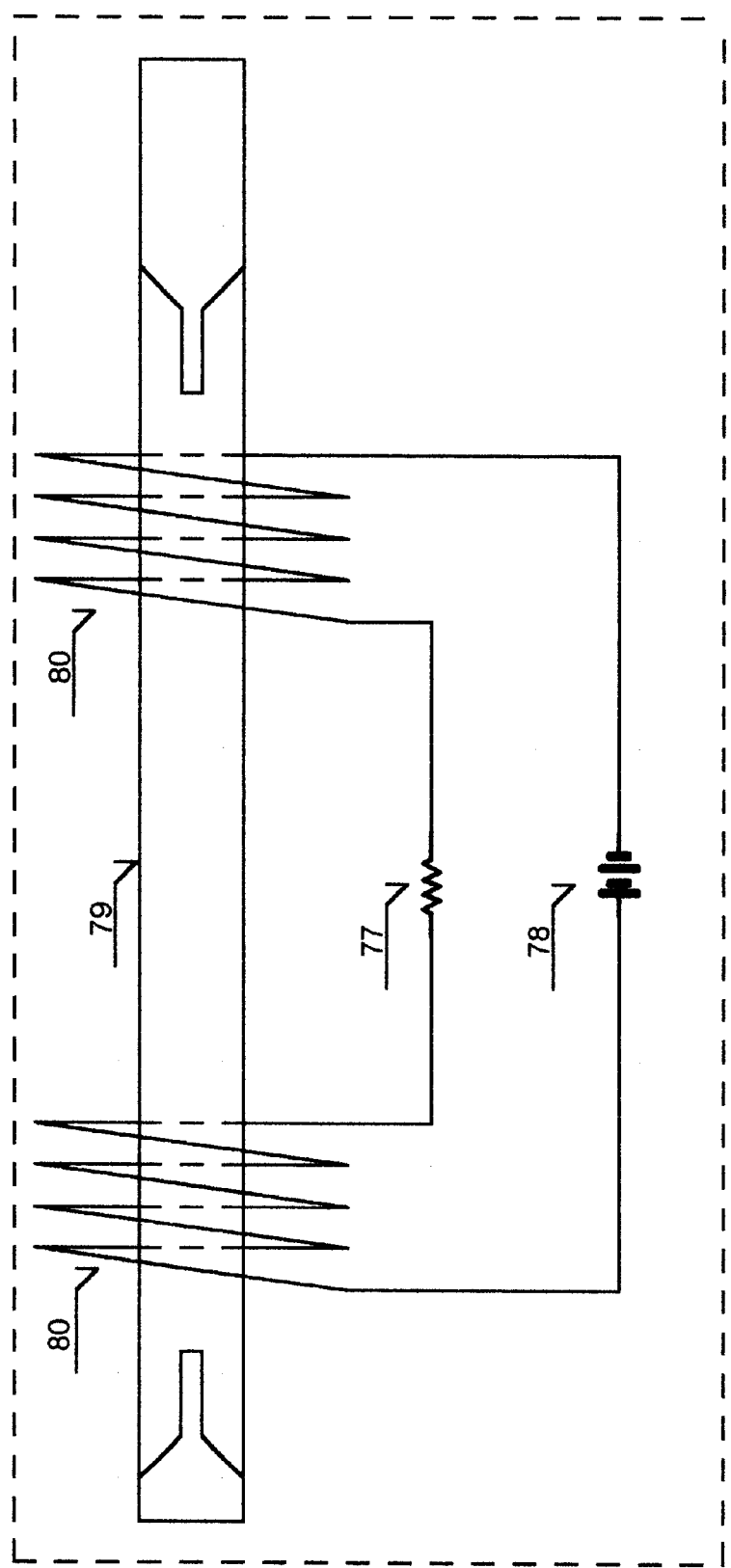
FIG. 13 illustrates the use of external windings to control arc within an x-ray tube.

FIG. 13 illustrates the use of external windings 80 to control the arc within the tube. According to Lenz's Law, the electromagnetic field in the tube will produce a current in the windings 80 that produces a field back on the tube 79 working against the motion of the tube current. This may lead to greater charge buildup in the plasma adjacent to the electrode, so when it does arc, the arc contains more charge. The circuit can be an active or passive design with the simplest being shown with a resistor 77 and a capacitor, or other voltage source or storage device 78 in the circuit. If the tube is driven in AC, the R-L-C circuit can be designed to resonate at the same frequency. The electrostatic field from the windings also helps keep the arc centered in the tube in the region within the windings.

According an embodiment of the invention using magnetic confinement, the frequency of the power supply can be adjusted such that it coincides with the arc timing and transformer resonance characteristics creating a resonant state within the tube and power supply. For example, the L8610 tube sustains an arc with a minimum duration of approximately 200 nanoseconds, so a power supply frequency in the 2 to 5 megahertz range would be required. The duration is largely a function of arc path length, and can vary from a few nanoseconds to a few milliseconds, and a resonant frequency can in theory be found over the entire range, given a suitable transformer and switching power supply. For this reason, the present invention may extend to higher frequencies when the arc durations are shorter, limited only by the ability to construct suitable high frequency, high voltage transformers. It is also possible to enhance the resonant effect and create high-pressure nodes periodically along the length of the tube where x-ray production would be quite high by tuning the Crooks bands spacing with the voltage and pressure such that the arc length is an integer multiple of the individual Crooks band spacing. The addition of electrostatic and/or magnetic confinement can further increase the intensity of interactions in the nodes by confining them to a smaller region of the tube.

Figure 11:
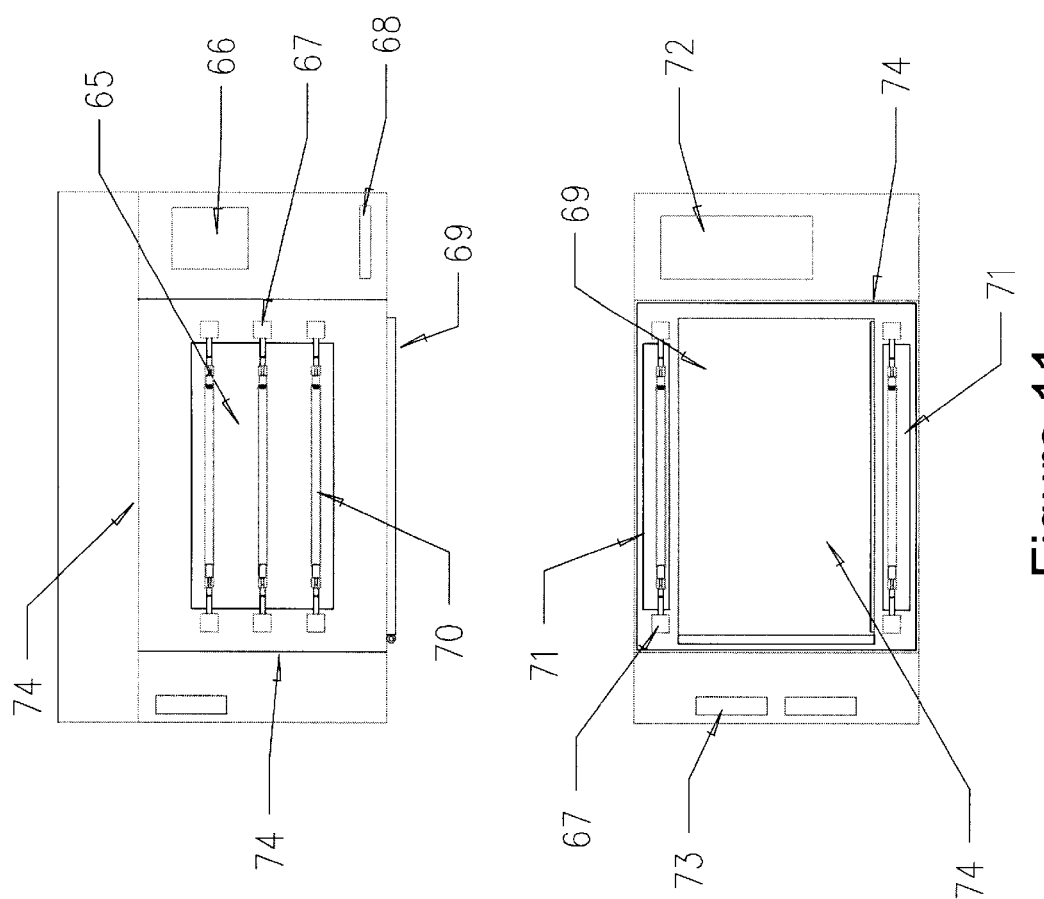
FIG. 11 illustrates an exemplary cabinet for the x-ray source according to an embodiment of the present invention.
Figure 12:
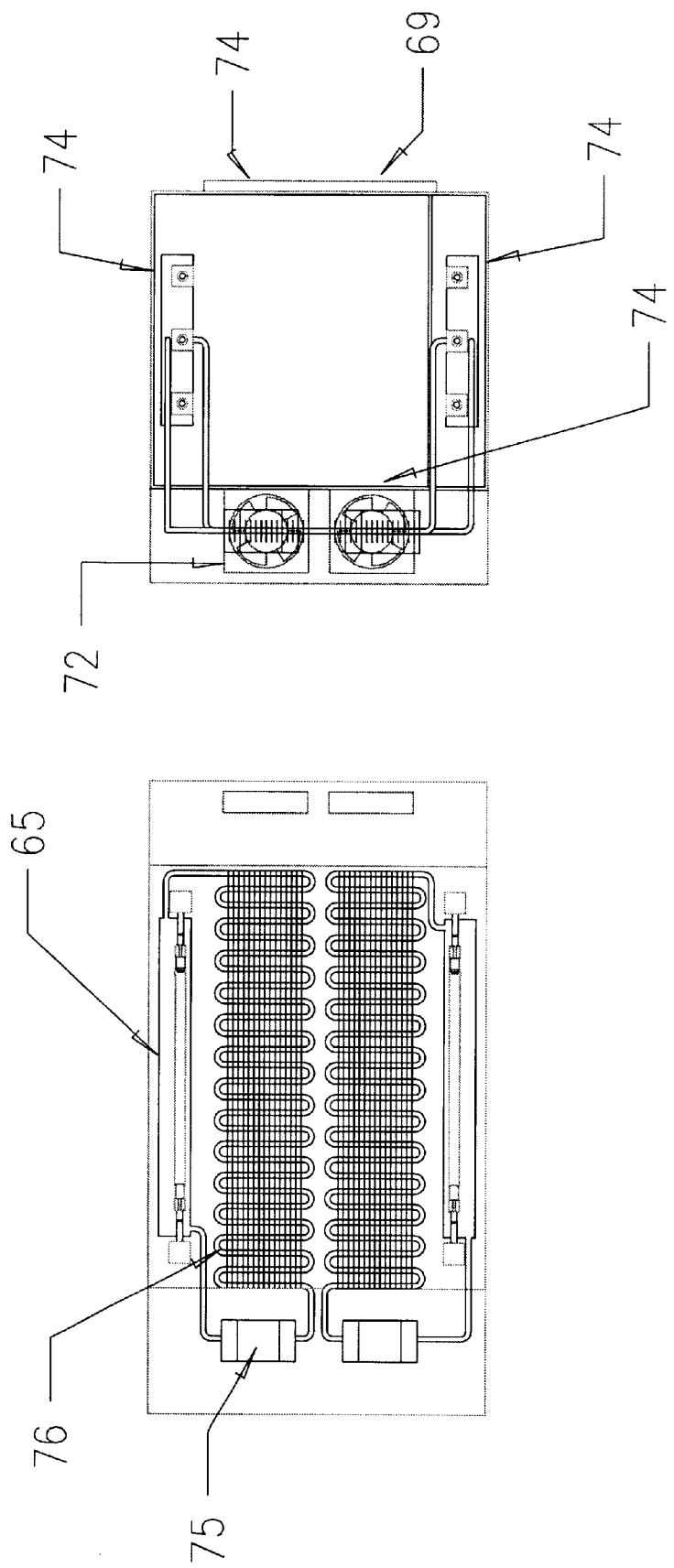
FIG. 12 illustrates another exemplary cabinet for the x-ray source according to another embodiment of the present invention.

In yet another embodiment of the invention, cooling of the tubes may be accomplished through convective or forced air cooling, or static or circulated liquid cooling. One of the most attractive options, and a predominant method used with high power x-ray tubes, is the use of a static or oil filled container that provides both cooling and electrical insulation. FIG. 11 illustrates an exemplary system with tubes 70 placed in oil-filled trays (65 and 71). FIG. 12 illustrates an alternate system that further includes a heat exchanger 76 and an oil pump 75 for running at higher power. Evaporative cooling techniques can be used as well and are particularly suitable for high power applications. For high-powered in-line systems a large heat exchanger may be incorporated with a circulated coolant design that can even be located outside a building to minimize heat buildup inside a structure.

Another aspect of the invention involves the selection of vapor used within the x-ray tube. The selection of the vapor relates to the particular application. In one example, for a fluorescent x-ray tube designed for irradiating meat up to 10–12 cm thick, 30 keV x-rays are attractive since as much as 80% of the x-ray flux hitting the meat will be absorbed. Accordingly, for this application, xenon, which has a characteristic K x-ray emission at about 30 keV, would be selected as the fill gas for the fluorescent x-ray tube. Several other gases are attractive for other applications. For instance, krypton would be useful, with its 13 keV x-ray emissions, for the irradiation of thinner and/or lower atomic number materials. A heavier vapor such as mercury (70 and 80 keV) would be suitable for thicker and/or higher atomic number or more dense materials such as steel. In each of the above cases, the operating voltage of the power supply must be adjusted accordingly. In general, the higher the atomic weight of the vapor the higher the characteristic x-ray energy, and the higher energy conversion efficiency. Other atoms present in other gases or gas mixtures used in lighting systems known to the art such as halogens, sodium, or various metal halides, would be suitable as well for special applications. Any element, or combination of elements, that form a suitable vapor may be used to obtain specific characteristic x-ray emission energies. Any mixtures of the above gases may also be suitable in order to change the energy spectrum. An additional quench gas such as noble gases or methane may be needed in some mixtures.

By designing the irradiation system of the present invention to produce radiation at several different energies it is possible to get better dose uniformity throughout the target material, particularly when it is thicker or higher in density. The irradiation system could use one tube filled with the required mixture of gases; or several tubes, each with a principally mono-species gas fill, could be used together as an irradiation package. In addition, the fill gas in the tubes may be designed to produce desired x-ray emissions of the K, L, M, or N transitions of certain fill gas elements that may useful separately, or in combinations.

In addition, in order to achieve x-ray production in a vapor filled tube, the vapor pressure must be very low, generally in the range of 0.01 to 100 millitorr depending on the desired voltage, fill gas, and tube construction. In this pressure range as the pressure is decreased the breakdown voltage of the vapor in the tube increases. Depending on tube construction, it will take from a few kV to a hundreds of kV to trigger the x-ray tube and give off x-rays. This method does however extend into the gamma ray range of energies as it is possible to make tubes with pressures in $10^{-6}$ to $10^{-4}$ torr range that require MeV energy power supplies.

In designing the present invention, the tube pressure and voltage should be matched, since if there is too little voltage for a given pressure there will only be a faint glow discharge across the tube. The glow discharge regime is a very inefficient and low power regime with regard to x-ray production. We have measured it and found it to be 25 to 100 times worse than a fluorescent x-ray tube designed in accordance with this invention or 5–10 times worse than even a traditional vacuum x-ray tube. If the pressure is too high for a given voltage, the tube will arc too soon and the x-ray energy will be lower than desired. While the arcs may be longer in duration, there will not be a very efficient conversion of energy into x-rays. In order to create x-rays efficiently, the pulse must be very fast, typically much less than a microsecond, so it is important for the voltage to be just high enough so an arc initializes, but current limited so that the vapor arc discharge is not sustained for very long. Experiments have shown that once the initial arc is established, which takes from 10's to 100's of nanoseconds depending on tube length, sustaining the arc leads to decreased x-ray yields. At the extreme limit, the discharges fall under the class of discharge phenomena called pseudosparks in which charges build up at one electrode until it becomes unstable and then arc across the tube, but there is insufficient current flow through the circuit to sustain the arc. Pseudosparks are also known as "hollow cathode discharge" since arc formation is enhanced by the presence of relatively sharp edges on the electrode. The simplest version of a "hollow cathode design is a hollow cylinder, but it may also be a large area plate where arcs form at the edges. The plate area may include holes in it to promote arc and thus x-ray development over a large surface area. In principle though, since pseudosparks are initiated in response to a free charge buildup near the electrode, designing an electrode with more surface area is beneficial. The present invention further contemplates to increasing the charge available for the arc by constructing an electrode in the form of multiple concentric cylinders. In alternate embodiments, the charge available may be increased by increasing the diameter or elongating the electrode.

Further, very short arcs are the most efficient mechanism for producing x-rays. In the absence of an electrode redesign or an external electromagnetic field generating device, the best way then to push more power through the tube is to increase the frequency, hence the development of a high frequency supply.

Figure 8:
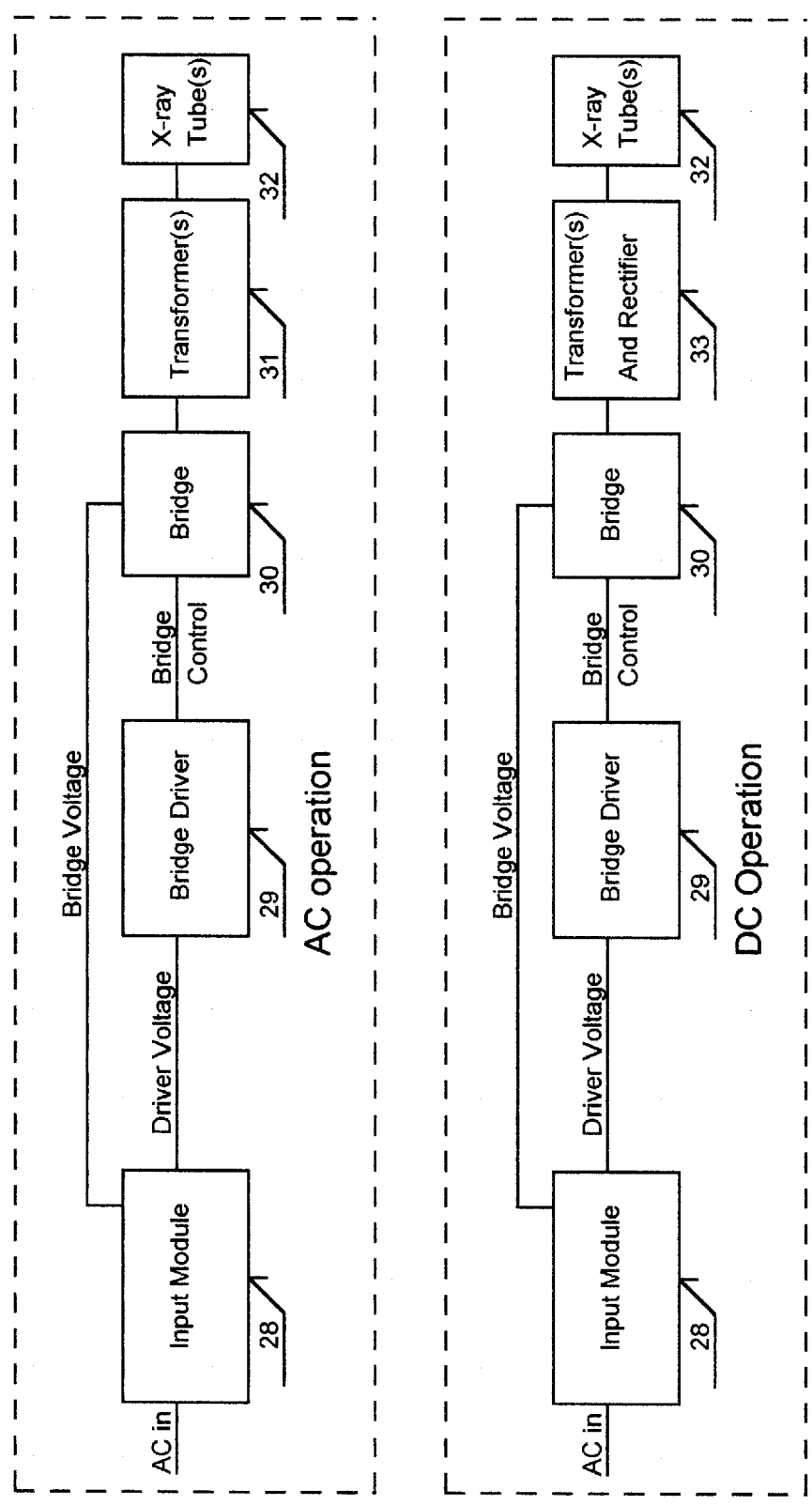
FIG. 8 shows a block diagram of the power supply components according to an embodiment of the present invention.

The present invention further contemplates the use of a high voltage resonant power supply to produce the vacuum arcs needed to drive the x-ray tube. The basic block diagram of a resonant AC power supply is shown in FIG. 8a. The direct current power module at the front end of the power supply may contain the power factor correction circuit with the primary voltage supply and also an auto ranging feature that permits operation at multiple common voltages and frequencies. For example, in one embodiment, the auto ranging feature would permit operation at 110V/60 Hz and 220V/50 Hz. They can be incorporated together into an input module 28. This primary voltage supply can be fixed or adjustable from a few volts to five kilovolts or more, and may be a battery, a linear supply or use buck, boost, or other common voltage conversion topologies. The direct current power module may also include a current control circuit. It will be used to drive the power supply's high frequency switching controller 29 and resonant power module 30 that make up the AC inverter. The high frequency resonant controller may in theory operate at a frequency from a few Hz to 100 MHz or more, but the preferred embodiment is in the 2 kHz to 10 MHz range due to the overall efficiency, resonant characteristics, and transformer operating frequencies. It is also useful in many cases to operate at frequencies above 20 kHz so as not to be in the audible range. The high frequency switching controller is also a possible location for both voltage and frequency control circuits either instead of or in addition to similar types of controls at the direct current power module. A transformer or transformers 31 are used to raise the voltage needed to power the x-ray tube 32. The higher the input voltage to the bridge, the lower the winding ratio in the transformer(s), and the better its performance and frequency range will be.

Figure 9:
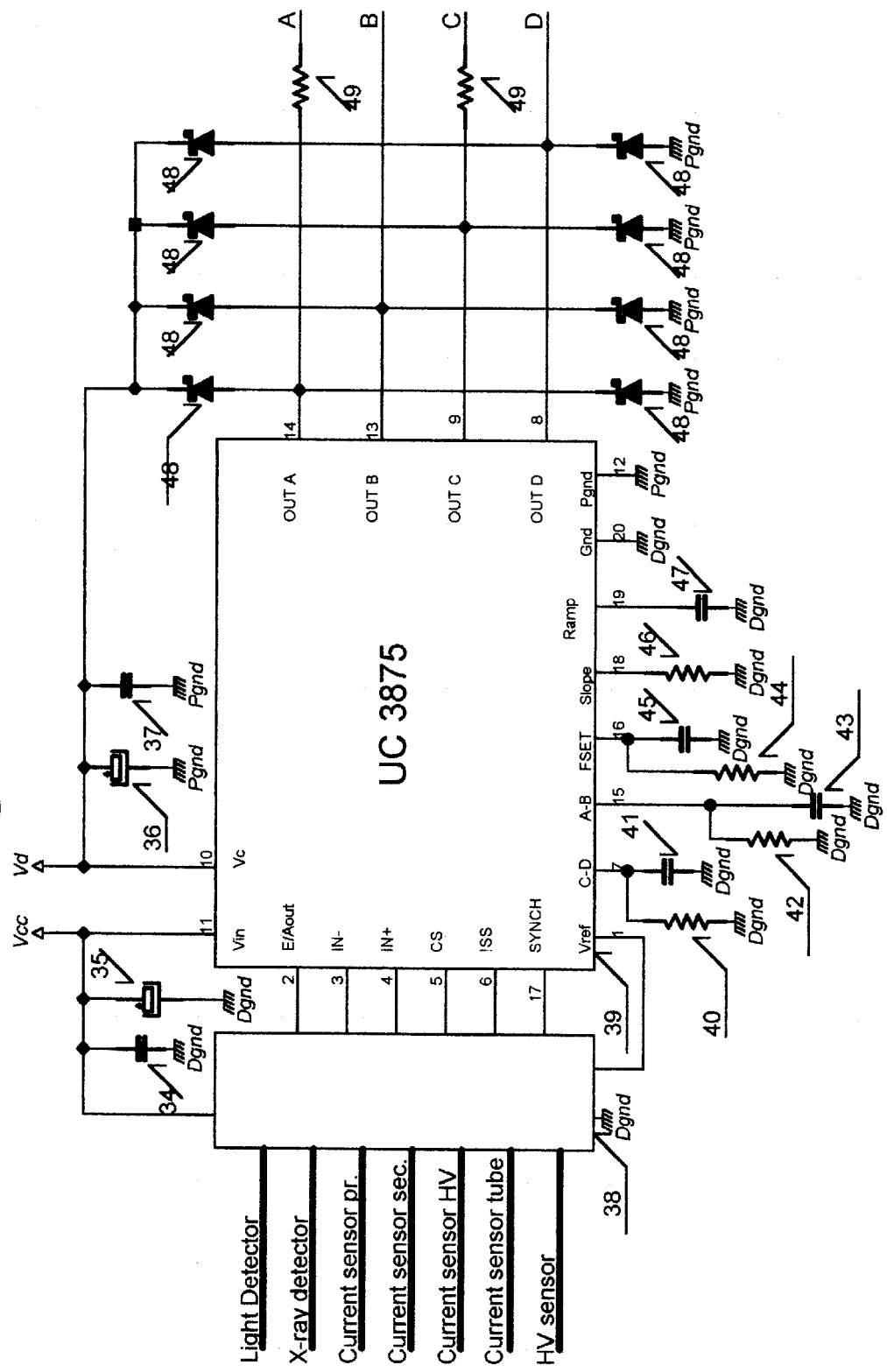
FIG. 9 is a schematic of a bridge driver for a resonant AC power supply according to the present invention.

FIG. 9 shows an exemplary simple circuit design for a high frequency switching controller or bridge driver 29 based on a Texas Instruments (formerly Unitrode) UC 3875 controller 39. Numerous other controllers and a variety of driver circuit designs are commonly available for driving resonant power supplies, and suitable versus may be adapted for use with the present invention.

Figure 10:
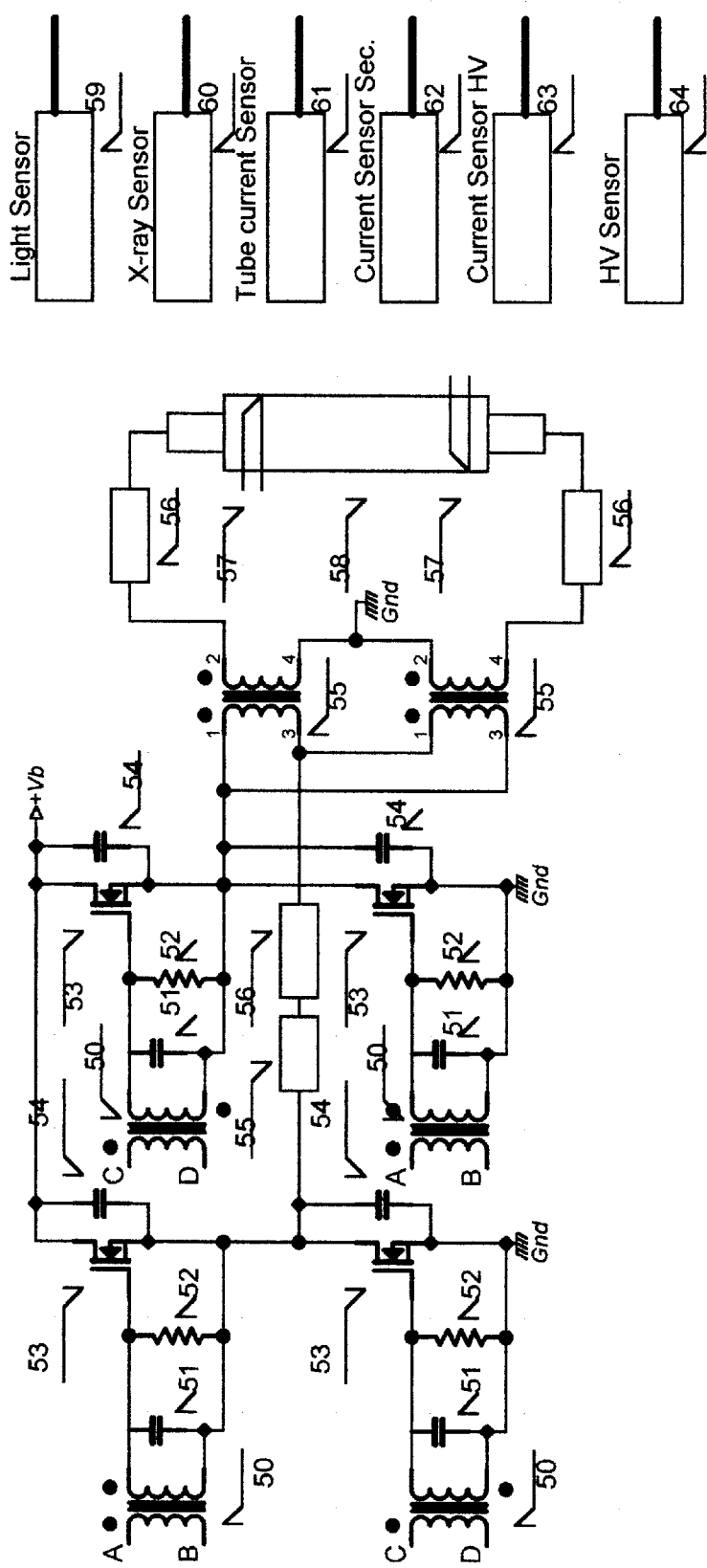
FIG. 10 is a schematic of a resonant bridge driver for an AC power supply according to another aspect of the present invention.

FIG. 10 is a more detailed diagram of the bridge driver 29 according to an aspect of the present invention. The resonant bridge circuit (50–58) includes transformers (55), ballasts (56), and a tube (58). The output of the H bridge is connected to two transformers 55. The primary windings are in antiphase, while the secondary windings are in series. This way the circuit, and more to the point, the high-voltage insulation has to be designed for only half of the required high voltage. This example inverter is a zero voltage switching resonant bridge. It is shown here with isolation transformers for driving the MOSFET's, but they may also be driven with optical coupling devices. A Royer power supply is another attractive topology commonly used in cold cathode plasma applications such as plasma displays, and it is also possible to base a design on a half bridge instead of a full or H bridge. It is also possible to use the push pull or other converter topology, but as with the half bridge they can only achieve half the voltage of the full bridge given the same level of voltage rating of the components.

A single transformer or two transformers with the primaries in phase may be used, but it would then have to be designed for twice the voltage, increasing both its size, expense, and design difficulty. Alternatively, a single transformer with two secondaries wound in opposite directions and wired in series may be used, but this design requires a core design that is not commonly available in an appropriate material for the required frequency range. It is also possible to have the primary and secondary windings on different legs of the core to make the high voltage insulation design easier, or they may be on the same leg to achieve better efficiency. In one specific embodiment the high voltage high frequency transformer design incorporates tubular insulators between winding layers made of Teflon, Kapton or other similarly good insulator to achieve insulation between layers rated anywhere from 20 to 250 kV DC allowing AC operation in the hundreds of kV. When properly designed, the transformers 55 act as the ballast in the circuit. It is possible to add other ballast components between the transformer(s) 55 and the tube as shown, but additional ballast components to diminish the x-ray intensity, and therefore may also be deleted.

Although similar power supplies have been designed for neon lights, the present design is used at higher voltages for the purpose of useable x-ray production while designing it in ways to yield arc characteristics that lead to enhanced x-ray output. High voltage and high power components that are desirable for the bridge, particularly the MOSFETs 53 and/or IGBTs, have only recently become available, but the primary design problem is the high-frequency, high-voltage transformer. The difficulty lays with the fact that a large area is needed inside the transformer core to accommodate the high voltage insulation, yet the larger the core the worse it performs at high frequency. A person of ordinary skill in the art of transformer design will be aware of the difficulties overcome after experimenting with a variety of cores, wire, and insulating materials.

The high frequency resonant power supply design of the present invention is much more efficient than the pulsed DC and capacitive discharge based designs common in flash tubes and plasma pinch devices. That is why most high voltage power supply manufacturers incorporate a resonant supply into their design, between the lower voltage stage and one or more voltage multipliers. But, to date, they are limited to approximately 10–20 kV due to the previously mentioned transformer design problems. Higher frequency means less energy needs to be transmitted through the tube per pulse allowing for smaller, more readily available, and faster components to be used in the power supply. This leads to a power supply that is easily one-tenth the cost of traditional DC supplies.

Although the present invention contemplates the use of a DC power supply design, a problem that exists with such a design is that the ionized atoms are accelerated toward the cathode and can damage it. Accordingly, the present invention further contemplates the use of an AC power supply. An AC power supply offers the advantage of spreading the damage between two electrodes, thus improving tube life.

As show in FIG. 8B, a related power supply design uses the resonant inverter at the front end with a rectifier 33, preferably a full wave bridge rectifier. This still yields efficient DC pulses to generate the arcs. A high voltage capacitor or capacitors can be used with the rectifier it to minimize the voltage drop between pulses. The voltage between pulses needs to drop to the point that the tube is in the glow discharge regime, and then increase again until a vapor arc (or pseudospark) is formed in the tube. The difference required is on the order of 5 kV to 15 kV. The negative side of this design is that the extra components need to be rated for high voltage making them somewhat expensive and hard to obtain, but it may still prove suitable for some applications.

Control of an embodiment of the power supply of the present invention may be accomplished with simple switches or sophisticated microprocessor control and programmed logic, depending on the extent of the operational control features that are required. Use of electro-optic isolation is also of obvious benefit in general with a high voltage apparatus. Safety interlocks that are required with any x-ray producing device may follow any of the typical designs.

FIG. 10 further illustrates the use of active feedback control as an optional means to maintain stable power supply output. In an embodiment, stability is maintained by measuring the radiation flux with a radiation detector 60 such as a Geiger-Mueller tube or pin diode, or any of a variety of light measuring devices 59 and using the resulting measurement to adjust the power supply output or on time to maintain consistent exposure. In addition, since a current and/or differential high voltage measurement can be used to determine the arc regime, active feedback control that adjusts the power supply output to maintain the desired arc characteristics can be accomplished via an active current measurement of either the primary or secondary current. As shown in FIG. 10, a current transformer 61 may measure the current in the tube. In addition, another current transformer 62 may be for measuring the current in the secondary winding. Finally, a current transformer 63 may measure current on the outside of the tube. The primary current can be most easily measured by measuring the current drop across a fixed resistance, but high voltage in the secondary side makes current monitoring much more difficult. In that case, devices such as a current transformer may be preferred over a series resistance. In the DC topology, it is possible to have a series resistance at ground potential to enable a measurement.

Presenting the material to be irradiated to the x-ray source can be accomplished in many ways traditional to industries such as x-ray fluorescence (XRF) analysis. It may be a closed cabinet device where material is placed in a cabinet that is then closed, and then safety interlocks are actuated to allow the irradiation process to be initiated. One example of a closed cabinet device could be very similar to a microwave oven both in terms of construction, safety interlocks, and controls, with one principle exception being the use of appropriate shielding for x-rays. X-ray tubes may be oriented above, below, to the sides, or in any combination that is suitable to and helps achieve uniform irradiation of the material.

FIGS. 11 and 12 illustrate exemplary closed-cabinet devices. These closed-cabinet devices could incorporate traditional microwave oven construction features such as safety interlocks and controls (68 and 72). In addition, these closed-cabinet devices would require additional shielding 74. As illustrated, an exemplary embodiment may use six fluorescent x-ray tubes 70 with two sets of three located in oil filed trays (65 and 71) above and below the sample chamber. A resonant power supply 66 supplies power. Each tube is in series with two high-voltage transformers/ballasts 67. The device may further include a microprocessor control board 68 and control interface such as a touch screen 72. A shielded door 69 opens and closes for easy access to the shielded chamber. The chamber is shielded on all sides with appropriate material such as lead. A cooling system may also be incorporated including cooling fans 73 that can either blow air across the tray 71 or across a heat exchanger 76. When using a heat exchanger 76, the heat exchanger 76 could be convective or use pumps 75 to circulate the oil.

Another embodiment of the present invention takes advantage of the small gains in performance that can be obtained by using reflected x-ray energy. X-rays are not efficiently scattered off of most materials so that the "reflected" energy is typically a factor of hundred times less than the incidence energy. There are some techniques that improve the efficiency, such as using materials that are easily excited by the incident X-rays and then fluoresce their own characteristic x-rays at a slightly lower energy. Such a material is functionally like a secondary target in XRF. In the example where xenon is the vapor used in the tube, a material such as tin (Sn) may be used as a secondary target/shield. The performance gain is small, but may be useful in some circumstances. It is also possible to enhance the reflectance by using low atomic number material such as hydrogenated material, since it is a superior x-ray scatterer to metals. It should be noted, however, that x-rays break the bonds in polymers, causing them to degrade over time. Therefore it is advisable to encapsulate such material. A third technique is to use materials that efficiently diffract the important x-ray energies; these types of materials are relatively expensive however and will likely increase the overall cost.

By using the fact that the "reflected" energy is low and it falls off with the square of the distance, it is also possible to produce x-ray devices that are open ended. One such familiar device is the airport luggage scanner. These types of configurations can be used for many in-line irradiation applications. And, for even more powerful x-ray systems, it is usually only necessary to force the x-rays to "reflect" off more surfaces before exiting the chamber to have it reach safe levels. This makes the material path a little more convoluted, but it is still practical in many cases. With liquid samples it is possible to have the fluid (such as water or juice) flow right past an appropriately insulated tube within piping, as is the case with many UV sterilization products.

A fluorescent x-ray tube is beneficial for applications in the x-ray fluorescence (XRF) industry as well. One significant problem in XRF is that the somewhat parallel beam from a typical x-ray tube will scatter off a sample being analyzed in such a way that the intensities at a given energy may be more due to surface features such as striations and diffraction phenomena rather than composition. The more randomized and broader beam inherent to some fluorescent x-ray tube designs can minimize this problem. Lower cost is also a major factor in making this technology useful in a broader class of applications.

By designing the tube with a short arc path, or with collimation, fluorescent x-ray tubes may also be used for industrial or radiographic imaging applications. The present invention may also be adapted to therapeutic applications as well. One example of which is a small diameter x-ray needle incorporating this technology that could be inserted into the body for the purpose of destroying cancerous tumors.

Due to the efficiency improvements offered by a plasma x-ray source, these types of sources have been studied extensively in relation to x-ray lithography applications where traditional x-ray tubes are generally not powerful enough, particularly when x-ray optical elements are incorporated in the design. The fluorescent x-ray tube of the present invention is also attractive for this application and may be configured as a broad beam source for simple contact masking techniques or as a smaller point source if the angular distribution from the source needs to be restricted. Various optical elements such as diffractive, multiplayer, or capillary optics could be used with this style of tube in the same fashion as they are used with other x-ray sources.

Fluorescent x-ray tubes may be incorporated into a device for the purpose or irradiating materials for the purpose of killing microorganisms or pests. The device may be used for the irradiation of materials such as food, water, and other beverages, and medical equipment or waste. It may be constructed in the form of a closed cabinet device, or an in-line device over or around a conveyance or within a liquid stream. The fluorescent x-ray tube is also suitable for other applications including but not limited to x-ray lithography, x-ray fluorescence, medical and industrial imaging and medical therapeutic devices.

Further, although the previously described high voltage, high frequency resonant power supply has been described in the context of x-ray production, the power supply according to the present invention may have other applications. For example, it is contemplated that the power supply is of equal value in other vacuum arc discharge applications. The present embodiment allows a better way of driving the following applications while still being able to operate as pseudo-DC power supply. With appropriate control features the power supply of the present invention can generate single pulses and mimic the DC supply with a HV switch or the DC supply with a capacitive discharge.

In one embodiment of the invention, the power supply can be used to produce vacuum arc discharges in vacuum arc deposition equipment designed to produce coatings. This equipment currently has similar limitations to other equipment previously mentioned in that they generally use a high voltage DC source and a capacitive discharge or other pulse forming system, and they have a pre-ionizing device to assist in triggering the arcs. The high voltage resonant power supply is lower in cost, more efficient and self trigger by over voltage. In addition, with a high frequency device, each arc can have much less charge, or in other words fewer ions, so it is possible to create much thinner and uniform coatings.

While at higher power that may be achieved with this power supply coatings can be produced much quicker or thicker than with lower frequency supplies.

In another embodiment it is envisioned that the power supply could be used in vacuum metal refining. Vacuum metal refining is used to improve uniformity and reduce grain size in alloys that otherwise would have overly large substructures. It is also used for degassing metals. The process works in much the same way as vacuum arc deposition in that material is vaporized and one location and electrically deposited by vacuum arc in another, but in vacuum metal refining the metal is deposited in a mold where an ingot is formed.

In still another embodiment it is envisioned that the power supply can be used in ion implantation devices. As mentioned previously, one of the technical challenges in designing a fluorescent x-ray tube was overcoming the tendency for the fill gas to be implanted into the electrode creating a reduction in vacuum. This property can be used to advantage in cases where ion implantation is used to change the properties of a material for applications such as wafer fabrication for solid-state devices. The basic operation and advantages are similar to the two previous types of equipment, but ion implantation requires even higher voltages, an area where the power supply designed for this invention would work exceptionally well.

Although the high voltage, high frequency resonant power supply for the production of x-rays has been described in the above-reference applications, it should be understood that the power supply described herein may be used in other applications without departing from the spirit and scope of the present invention.

While the invention may be adaptable to various modifications and alternative forms, specific embodiments have been shown by way of example and described herein. However, it should be understood that the invention is not intended to be limited to the particular disclosed embodiments. Rather, the invention is to cover all modifications, equivalents, and alternatives falling within the spirit and scope of the invention as defined by the claims. Moreover, the different aspects of the disclosed system and methods may be utilized in various combinations and/or independently.

What is claimed is:

1. A high-voltage high-frequency resonant power supply suitable for forming a resonant circuit with a vacuum envelope having two electrodes, such power supply comprising:
   a high-voltage high-frequency transformer;
   a resonant power module for creating a resonant circuit with the high-voltage high-frequency transformer;
   a high-frequency switching controller for controlling the resonant power module; and
   a direct current power module for supplying a D.C. voltage to the high frequency switching controller and the resonant power module.

2. The apparatus in claim 1 wherein the resonant power supply operates in the 2 kHz to 10 MHz frequency range.

3. The apparatus in claim 1 wherein the resonant power supply operates in the 10 kilovolt to 1 megavolt range.

4. The apparatus in claim 1 wherein the direct current power module produces 12 to 5000 volts.

5. The apparatus in claim 1 wherein the direct current power module is a battery.

6. The apparatus in claim 1 wherein the direct current power module is a rectifier assembly.

7. The apparatus in claim 1 wherein the direct current power module incorporates power factor correction.

8. The apparatus in claim 1 wherein the direct current power module incorporates an auto ranging feature.

9. The apparatus in claim 1 wherein the direct current power module incorporates voltage conversion.

10. The apparatus in claim 1 wherein the direct current power module incorporates a voltage control circuit.

11. The apparatus in claim 1 wherein the direct current power module incorporates a current control circuit.

12. The apparatus in claim 1 wherein the switching controller incorporates a voltage control circuit.

13. The apparatus in claim 1 wherein the switching controller incorporates a current control circuit.

14. The apparatus in claim 1 wherein the switching controller incorporates zero voltage switching.

15. The apparatus in claim 1 wherein the resonant power module is a full bridge.

16. The apparatus in claim 1 wherein the resonant power module is a half bridge.

17. The apparatus in claim 1 wherein the resonant power module is a push-pull topology.

18. The apparatus in claim 1 wherein the switching controller interfaces with the resonant power module using isolation transformers for driving the switching devices.

19. The apparatus in claim 1 wherein the switching controller interfaces with the resonant power module using optical coupling for driving the switching devices.

20. The apparatus in claim 1 wherein the switching controller drives two or more high-voltage transformers in parallel.

21. The apparatus in claim 1 wherein the switching controller drives two high-voltage transformers in anti-phase.

22. The apparatus in claim 1 wherein the switching controller drives two modules of two high-voltage transformers in anti-phase.

23. The apparatus in claim 1 wherein the high-voltage high-frequency transformer has primary and secondary windings on different legs of the core.

24. The apparatus in claim 1 wherein the high-voltage high-frequency transformer has primary and secondary windings on the same leg of the core.

25. The apparatus in claim 1 wherein the high-voltage high-frequency transformer has two secondary windings wound in opposite directions.

26. The apparatus in claim 1 wherein the high-voltage high-frequency transformer is constructed with the use of tubular insulation materials between winding layers.

27. The apparatus in claim 1 wherein the high-voltage high-frequency transformer drives a second higher voltage high frequency transformer.

28. The apparatus in claim 1 wherein the output of the high frequency transformer is rectified producing high-frequency direct current pulses.

29. The apparatus in claim 28 wherein the high frequency direct current pulses are smoothed through the use of capacitors.

30. The apparatus in claim 1 wherein the resonant power module is a Royer topology.

31. An apparatus for producing vacuum arc discharges comprising:
   a high-voltage high-frequency resonant power supply comprising:
     a high-voltage high-frequency transformer;
     a resonant power module for creating a resonant circuit with the high-voltage high-frequency transformer;

a high-frequency switching controller for controlling the resonant power module;

a direct current power module for supplying a D.C. voltage to the high frequency switching controller and the resonant power module; and a vacuum envelope with two electrodes, wherein the resonant power supply and the vacuum envelope with two electrodes are adapted to form a resonant circuit.

32. The apparatus in claim 31 wherein the vacuum arc discharges are used for vacuum arc deposition of coatings.

33. The apparatus in claim 31 wherein the vacuum arc discharges are used for vacuum metal refining.

34. The apparatus in claim 31 wherein the vacuum arc discharges are used for ion implantation.

35. The apparatus in claim 31 wherein the vacuum arc discharges are used for x-ray production.

36. The apparatus in claim 31 wherein the vacuum arc discharges are pseudosparks.

* * * * *

UNITED STATES PATENT AND TRADEMARK OFFICE
CERTIFICATE OF CORRECTION

PATENT NO.   : 6,630,799 B2                                                                     Page 1 of 1
DATED        : October 7, 2003
INVENTOR(S)  : Ray Fleming and Constantin Popa It is certified that error appears in the above-identified patent and that said Letters Patent is hereby corrected as shown below:

<u>Column 22,</u>
Lines 7-8, claim 36 should read:

36. The apparatus in claim 31 wherein the vacuum arc discharges are pseudosparks.

Signed and Sealed this

Second Day of December, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,630,799 B2
DATED         : October 7, 2003
INVENTOR(S)   : Ray Fleming It is certified that error appears in the above-identified patent and that said Letters Patent is hereby corrected as shown below:

Title page,
Item [56], References Cited, U.S. PATENT DOCUMENTS, "4,504,895 to Steigerwald" was considered by the Examiner.

Signed and Sealed this

Twenty-seventh Day of July, 2004

JON W. DUDAS
*Acting Director of the United States Patent and Trademark Office*